United States Patent [19]
Mouithys-Mickalad et al.

[11] Patent Number: 5,534,511
[45] Date of Patent: Jul. 9, 1996

[54] AMINOALKYL BENZOXAZOLINONES AND BENZOTHIAZOLINONES

[75] Inventors: Ange Mouithys-Mickalad, Loos; Patrick Depreux, Armentieres; Daniel Lesieur, Gondecourt; Gérard Adam, Le Mesnil Le Roi; Daniel-Henri Caignard, Paris; Pierre Renard, Versailles; Marie-Claire Rettori, Courbevoie, all of France

[73] Assignee: Adir et Compagnie, Courbevoie, France

[21] Appl. No.: 407,238

[22] Filed: Mar. 21, 1995

[30] Foreign Application Priority Data

Mar. 22, 1994 [FR] France ................... 94 03298

[51] Int. Cl.$^6$ ........................ A61K 31/55; C07D 403/00
[52] U.S. Cl. ................ 514/212; 540/603; 514/321; 514/367; 514/375; 546/197; 548/165; 548/221
[58] Field of Search .................. 540/603; 514/212

[56] References Cited

U.S. PATENT DOCUMENTS

| | | | |
|---|---|---|---|
| 4,554,284 | 11/1985 | Stringer et al. | 514/367 |
| 4,558,060 | 12/1985 | Caignard et al. | 514/375 |
| 4,831,031 | 5/1989 | Lune, III et al. | 514/254 |
| 5,225,409 | 4/1993 | Taverne et al. | 514/230.5 |
| 5,322,849 | 6/1994 | Yous et al. | 514/321 |
| 5,326,775 | 7/1994 | Yous et al. | 514/375 |

FOREIGN PATENT DOCUMENTS

| | | |
|---|---|---|
| 110781 | 6/1984 | European Pat. Off. |
| 478446 | 4/1992 | European Pat. Off. |
| 506539 | 9/1992 | European Pat. Off. |

*Primary Examiner*—Cecilia Tsang
*Attorney, Agent, or Firm*—Gordon W. Hueschen

[57] ABSTRACT

The invention relates to a compound selected from those of formula (I):

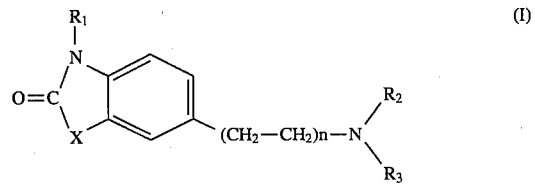

in which $R_1$, $R_2$, $R_3$, X and n are as defined in the description, the optical isomers thereof, and the addition salts thereof with a pharmaceutically acceptable acid or base and medicinal product containing the same, useful for treating a mammal afflicted with a pathology associated with the sigma receptors.

5 Claims, No Drawings

AMINOALKYL BENZOXAZOLINONES AND BENZOTHIAZOLINONES

The present invention relates to novel aminoalkyl benzoxazolinones and benzothiazolinones, to a process for their preparation and to the pharmaceutical compositions which contain them.

Patent Application EP 506,539 describes N-[(acylamino)ethyl] benzoxazolinone compounds as agents for modulating melatonin synthesis.

Patent Application EP 478,446 describes (aminoalkyl)benzothiazolinone compounds as antipsychotic agents, analgesics and anxiolytic agents.

The Applicant has now discovered novel aminoalkyl benzoxazolinones and benzothiazolinones which possess, surprisingly, a much more intense affinity for the sigma (σ) receptors than the compounds of Application EP 478,446.

The very high affinity of the compounds of the invention for the sigma receptors, which is markedly greater than that obtained with the compounds of Application EP 478,446, allows them to be used in the prevention and treatment of diseases linked to receptors of this type, namely, psychotic disorders, neuronal protection, memory disorders, cerebral circulatory insufficiency in elderly persons, Alzheimer's disease, inflammatory diseases of immune type such as arthritis, acute arthritis or chronic arthritis, and intestinal peristaltis disorders.

Moreover, the high selectivity of the compounds of the present invention for the sigma receptors, in particular their absence of affinity for the $D_2$ receptors, allows them to be used therapeutically with increased safety. In particular, the side effects of extrapyramidal type which are encountered during treatment using products with a high $D_2$ component, to which these effects are attributed, are not found with the products of the invention which, on average, have a 100 to 1000 times lower affinity for the $D_2$ receptors than do the compounds of Application EP 478,446. On balance, the products of the present invention have a selectivity ratio (sigma receptor affinity): ($D_2$ receptor affinity) 10,000 to 100,000 times greater than that obtained with the compounds of Application EP 478,446, thereby considerably enhancing their safety of use.

More particularly, the present invention relates to the compounds of formula (I):

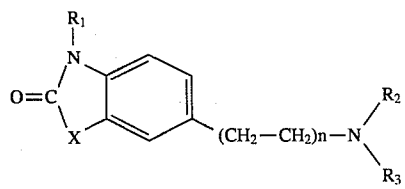

in which:
$R_1$ represents a hydrogen or an alkyl,
n represents 1 or 2,
X represents an oxygen or a sulfur,
$R_2$ represents a hydrogen or an alkyl,
and $R_3$ represents the group —$(CH_2)_m$—$R_4$ in which:
m represents 1,2, 3 or 4,
and $R_4$ represents a cycloalkylamino, dicycloalkylamino, N-cycloalkyl-N-alkylamino group or a heterocyclic radical of formula:

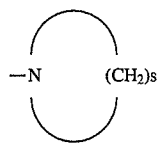

(where s is an integer between 4 and 8 inclusively), which is unsubstituted or substituted with an aryl, arylalkyl, substituted aryl or substituted arylalkyl group, or alternatively $R_2$ forms, with $R_3$ and the nitrogen atom which bears them, a group:

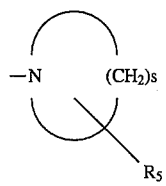

(where s is an integer between 4 and 8 inclusively), which is substituted with a substituent $R_5$ chosen from aryl, arylalkyl, substituted aryl and substituted arylalkyl,
the term "substituted", used in reference to the "aryl" and "arylalkyl" radicals, meaning that these groups are substituted with one or more groups chosen from halogen, alkyl, hydroxyl, alkoxy and trifluoromethyl,
the terms "alkyl" and "alkoxy" denote linear or branched groups containing from 1 to 6 carbon atoms,
the term "aryl" represents a phenyl or naphthyl group,
the term "cycloalkyl" denotes a group of 3 to 9 carbon atoms,
the optical isomers thereof and the addition salts thereof with a pharmaceutically acceptable acid and, when $R_1$ represents a hydrogen atom, with a pharmaceutically acceptable base.

The invention particularly relates to the compounds of formula (I) in which X represents a sulfur.

The invention particularly relates to the compounds in which $R_2$ forms, with $R_3$ and the nitrogen atom which bears them, a group:

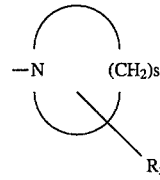

in which $R_5$ and s are as defined in formula (I).

Among the pharmaceutically acceptable acids which may be used to form an addition salt with the compounds of the invention, non-limiting examples which may be mentioned are hydrochloric acid, sulfuric acid, phosphoric acid, tartaric acid, malic acid, maleic acid, fumaric acid, oxalic acid, methanesulfonic acid, ethanesulfonic acid, camphoric acid and citric acid.

Among the pharmaceutically acceptable bases which may be used to form an addition salt with the compounds of the invention, non-limiting examples which may be mentioned are sodium hydroxide, potassium hydroxide, calcium hydroxide or aluminum hydroxide, alkali metal or alkaline-earth metal carbonates, and organic bases such as triethylamine, benzylamine, diethanolamine, tert-butylamine, dicyclohexylamine and arginine.

The alkyl radicals present in formula (I) may particularly be chosen from methyl, ethyl, n-propyl, isopropyl, n-butyl, isobutyl, sec-butyl, tert-butyl, pentyl or hexyl.

The alkoxy radicals present in formula (I) may be chosen from methoxy, ethoxy, n-propoxy, isopropoxy, n-butoxy, isobutoxy, sec-butoxy, tert-butoxy, pentyloxy and hexyloxy.

The halogens present in formula (I) may be chosen from bromine, chlorine, fluorine and iodine.

The invention preferably relates to the following compounds:

3-methyl-6-[2-(4-benzylpiperid-1-yl)ethyl]benzothiazolinone, 3-methyl-6-{2-[N-methyl-N-(2-piperid-1-yl-ethyl)amino]ethyl}benzothiazolinone, 3-methyl-6-[2-(4-phenylpiperid-1-yl)ethyl]benzothiazolinone, 3-methyl-6-[4-(4-benzylpiperid-1-yl)-n-but-1-yl]benzothiazolinone, 3-methyl-6-{2-{N-methyl-N-[2-(perhydroazepin-1-yl)ethyl]amino}ethyl}benzothiazolinone, 3-methyl-6-[4-(4-phenylpiperid-1-yl)-n-but-1-yl]benzothiazolinone, 3-methyl-6-{4-N-methyl-N-(2-piperid-1-ylethyl)amino]-n-but-1-yl}benzothiazolinone, 3-methyl-6-{4-{N-methyl-N-[2-(perhydroazepin-1-yl)ethyl]amino}-n-but-1-yl}benzothiazolinone, 3-methyl-6-{2-{N-methyl-N-[2-(1-pyrrolidin-1-yl)ethyl]amino}ethyl}benzothiazolinone, 3-methyl-6-{4-{N-methyl-N-[2-(1-pyrrolidin-1-yl)ethyl]amino}n-but-1-yl}benzothiazolinone.

The invention also covers the process for the preparation of the compounds of formula (I), wherein a compound of formula (II) is introduced into a suitable solution:

$$\text{(II)}$$

in which X, $R_1$ and n are as defined in formula (I) and Hal is a halogen atom, which compound is condensed
either with a compound of formula (III):

$$R_2\!-\!\!HN\!-\!(CH_2)_m\!-\!R_4 \quad \text{(III)}$$

in which $R_2$, $R_4$ and m are as defined in formula (I), to give a compound of formula (Ia):

$$\text{(Ia)}$$

in which X, $R_1$, $R_2$, $R_4$, n and m are as defined above, or with a compound of formula (IV):

$$\text{(IV)}$$

in which $R_5$ and s are as defined in formula (I), to give a compound of formula (Ib):

$$\text{(Ib)}$$

in which X, $R_1$, $R_5$ and s are as defined above, which compounds of formula (I) may, if so desired, be purified according to one or more purification methods chosen from crystallization, chromatography on silica gel, extraction, filtration and passing over charcoal or resin, separated, where appropriate, into the possible optical isomers thereof, or salified with a pharmaceutically acceptable acid or base.

The invention also relates to the process for the preparation of the compounds of formula (Ia) as defined above, wherein a compound of formula (V):

$$\text{(V)}$$

in which X, $R_1$, $R_2$, m and n are as defined in formula (I), is treated successively with one or more halogenating agents, to give a compound of formula (VI):

$$\text{(VI)}$$

in which X, $R_1$, $R_2$, m and n are as defined above and Hal' represents a halogen atom, which compound is reacted with a compound of formula (VII):

$$H\!-\!R_4 \quad \text{(VII)}$$

in which $R_4$ is as defined in formula (I), to give a compound of formula (Ia) as defined above, which compounds of formula (Ia) may, if so desired, be purified according to one or more purification methods chosen from crystallization, chromatography on silica gel, extraction, filtration and passing over charcoal or resin, separated, where appropriate, into the possible optical isomers thereof, or salified with a pharmaceutically acceptable acid or base.

The invention also covers the process for the preparation of the compounds of formula (Ia) as defined above, wherein a compound of formula (VIII):

$$\text{(VIII)}$$

in which $R_1$, $R_2$, X and n are as defined in formula (I), is condensed with a compound of formula (IX):

Hal"—(CH$_2$)$_m$—R$_4$   (IX)

in which R$_4$ and m are as defined in formula (I) and Hal" represents a halogen atom, to give a compound of formula (Ia) as defined above, which compounds of formula (Ia) may, if so desired, be purified according to one or more purification methods chosen from crystallization, chromatography on silica gel, extraction, filtration and passing over charcoal or resin, separated, where appropriate, into the possible optical isomers thereof, or salified with a pharmaceutically acceptable acid or base.

The invention also relates to the compounds of formula (V):

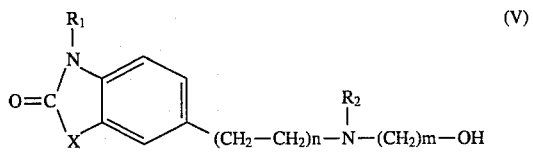

in which X, R$_1$, R$_2$, m and n are as defined in formula (I), and the compounds of formula (VI):

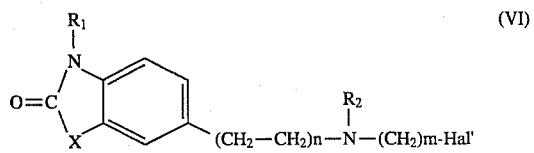

in which X, R$_1$, R$_2$, m and n are as defined in formula (I) and Hal' represents a halogen atom, which compounds are useful as intermediates in synthesis of compounds of formula (I).

The starting materials used in the processes described above are either commercial or are readily accessible to those skilled in the art according to processes which are well known in the literature. Reference will more particularly be made, for the compounds of formula (II), to the descriptions in Patent Applications EP 478,446 and EP 506,539.

The compounds of formula (I) possess very valuable pharmacological properties.

The very high affinity of the compounds of the invention for the receptors sigma do them useful for treating motor disorders such as dystonia (walker, J.M.: Drug specifity of pharmacology dystonia, Pharmacol. Biochem. Behav. 1990, 36, 151), tardive dyskinesia (Lindstrom, L. H.: Acta Psychiatr. Scand. 1988, 77, 1122), psychotic disorders (Chouinard, F., Annable, L. Psychopharmacology 1984, 84, 282), and in the treatment of damage in connection with peripheral or cerebral ischemia, states of shock (Pontecorvo, M. J., Brain Res. Bull. 1991, 26, 461), cerebral circulatory insufficiency, Alzheimer's disease and the regulation of immune phenomena (Carroll, F. I., Med. Chem. Res. 1992 2, 3), the treatment of addiction to cocaine (Abou—Gharbia, M., Academic. Press. Inc. Bristol. J. Ed. Publisher, 1993, 28, 1), the diagnosis and localization of tumors (Hudzik, T. J., Psychopharmacology, 1992, 108, 115; Abou—Gharbia, M., Academic. Press. Inc. Bristol. J. Ed. Publisher 1993, 28, 1) and vomiting (Hudzik, T. J., Eur. J. Pharmacol, 1993, 2;36, 279)) as well as in the treatment of inflammatory diseases of immune origin, intestinal motility disorders and chronic or acute arthritis.

The subject of the present invention is also the pharmaceutical compositions containing the compounds of formula (I) or, where appropriate, one of the addition salts thereof with a pharmaceutically acceptable acid or base, in combination with one or more excipients.

Among the pharmaceutical compositions according to the invention, mention may more particularly be made to those which are suitable for oral, parenteral, nasal, per- or transcutaneous, rectal, perlingual, ocular or respiratory administration and especially simple or sugar-coated tablets, sublingual tablets, sachets, packets, gelatin capsules, glossettes, lozenges, suppositories, creams, ointments, dermal gels and drinkable or injectable ampules.

The dosage varies depending on the sex, age and weight of the patient, the route of administration, the nature of the therapeutic indication or on the treatments possibly in combination, and is graduated between 0.01 mg and 100 mg, and more particularly 0.1 to 10 mg, taken once or twice per 24 hours.

The examples which follow illustrate the invention.

The $^1$H nuclear magnetic resonance spectra were acquired using TMS (tetramethylsilane) as internal reference. The chemical shifts are expressed in parts per million (ppm). The infrared spectra were acquired in the form of potassium bromide pastilles containing approximately 1% of the product to be analyzed.

PREPARATION 1:
3-METHYL-6-(2-PHTHALIMIDOETHYL) BENZOTHIAZOLINONE

Reactants:

| | |
|---|---|
| 3-Methyl-6-(2-bromoethyl)-benzothiazolinone | 0.01 mol (2.72 g) |
| Potassium phthalimide | 0.01 mol (1.85 g) |
| Anhydrous dimethylformamide | 25 cm$^3$ |

Procedure:

Into a ground-necked flask fitted with a water-condenser and containing 0.01 mol of potassium phthalimide in 20 cm$^3$ of dimethylformamide is added dropwise 0.01 mol of 3-methyl-6-(2-bromoethyl)benzothiazolinone which is pre-dissolved in 5 cm$^3$ of anhydrous dimethylformamide.

The mixture is heated at reflux for one hour.

The reaction mixture is allowed to cool and is then poured into ice-water.

The precipitate obtained is washed several times with water, drained, dried and then recrystallized.

| | |
|---|---|
| Molecular weight: | 338.30 g.mol$^{-1}$ |
| Melting point: | >260° C. |
| Yield | 60% |
| Recrystallization solvent | dimethylformamide |

PREPARATION 2:
3-METHYL-6-(4-PHTHALIMIDOBUTYL) BENZOTHIAZOLINONE

Reactants:

| | |
|---|---|
| 3-Methyl-6-(4-bromobutyl)-benzothiazolinone | 0.01 mol (3.00 g) |
| Potassium phthalimide | 0.01 mol (1.85 g) |
| Dimethylformamide | 25 cm$^3$ |

Procedure:

The procedure is identical to that used to obtain the compound described in Preparation 1.

| | |
|---|---|
| Molecular weight: | 366.36 g.mol$^{-1}$ |
| Melting point: | 159–160° C. |
| Yield | 56% |
| Recrystallization solvent | 95° alcohol |

PREPARATION 3:
3-METHYL-6-(2-AMINOETHYL) BENZOTHIAZOLINONE HYDROCHLORIDE

Reactants:

| | |
|---|---|
| 3-Methyl-6-(2-phthalimido-ethyl)benzothiazolinone | 0.01 mol (3.38 g) |
| Hydrazine hydrate | 0.01 mol (4.85 g) |
| 95° Alcohol | 100 cm$^3$ |

Procedure:

0.01 mol of 3-methyl-6-(2-phthalimidoethyl)benzothiazolinone is heated to reflux in 100 cm$^3$ of 95° alcohol.

0.1 mol of hydrazine hydrate are added dropwise. The reflux is maintained for three hours.

The alcohol is evaporated off. The residue is taken up in 50 cm$^3$ of water and extracted three times with 50 cm$^3$ of chloroform. The chloroform phases are dried over calcium chloride and are then evaporated under reduced pressure.

The residue is taken up in 50 cm$^3$ of absolute ethanol and is sparged with a stream of gaseous hydrogen chloride. The precipitate formed is drained and recrystallized.

| | |
|---|---|
| Molecular weight | 244.75 g.mol$^{-1}$ for C$_{10}$H$_{13}$ClN$_2$OS |
| Melting point: | 228–230° C. |
| Yield | 72% |
| Recrystallization solvent | absolute alcohol |

PREPARATION 4:
3-METHYL-6-(4-AMINOBUTYL) BENZOTHIAZOLINONE HYDROCHLORIDE

Reactants:

| | |
|---|---|
| 3-Methyl-6-(4-phthalimido-butyl)benzothiazolinone | 0.01 mol (3.66 g) |
| Hydrazine hydrate | 0.01 mol (4.85 cm$^3$) |
| 95° Alcohol | 100 cm$^3$ |

Procedure:

The procedure is identical to that used to obtain the compound described in Preparation 3.

| | |
|---|---|
| Molecular weight | 272.80 g.mol$^{-1}$ |
| Melting point | 214–215° C. |
| Yield | 82% |
| Recrystallization solvent | absolute alcohol |

PREPARATION 5:
3-METHYL-6-(2-TRIFLUOROACETAMIDOETHYL) BENZOTHIAZOLINONE

Reactants:

| | |
|---|---|
| 3-Methyl-6-(2-aminoethyl)-benzothiazolinone hydrochloride | 0.010 mol (2.44 g) |
| Trifluoroacetic anhydride | 0.012 mol (1.70 cm$^3$) |
| Anhydrous pyridine | 50 cm$^3$ |

Procedure:

0.010 mol of 3-methyl-6-(2-aminoethyl)benzothiazolinone is dissolved in 50 cm$^3$ of anhydrous pyridine in a 100 cm$^3$ round-bottomed flask.

The reaction mixture is cooled in an ice bath and 0.012 mol of trifluoroacetic anhydride is added dropwise with magnetic stirring.

The mixture is left stirring for 30 minutes at room temperature.

The reaction mixture is poured into ice-water and the precipitate formed is drained, washed with water, dried and then recrystallized.

| | |
|---|---|
| Molecular weight | 304.22 g.mol$^{-1}$ |
| Melting point | 156–158° C. |
| Yield | 97% |
| Recrystallization solvent | cyclohexane |

PREPARATION 6:
3-METHYL-6-(4-TRIFLUOROACETAMIDOBUTYL) BENZOTHIAZOLINONE

Reactants:

| | |
|---|---|
| 3-Methyl-6-(4-aminobutyl)-benzothiazolinone hydrochloride | 0.010 mol (2.72 g) |
| Trifluoroacetic anhydride | 0.012 mol (1.70 cm$^3$) |
| Anhydrous pyridine | 50 cm$^3$ |

Procedure:

The procedure is identical to that used to obtain the compound described in Preparation 5.

| | |
|---|---|
| Molecular weight | 332.27 g.mol$^{-1}$ |
| Melting point | 114–115° C. |
| Yield | 98% |
| Recrystallization solvent | cyclohexane |

PREPARATION 7: 3-METHYL-6-[2-(N-METHYLTRIFLUOROACETAMIDO) ETHYL)BENZOTHIAZOLINONE

Reactants:

| | |
|---|---|
| 3-Methyl-6-(2-trifluoroacet-amidoethyl)benzothiazolinone | 0.01 mol (3.10 g) |
| Potassium carbonate | 0.04 mol (5.50 g) |
| Methyl iodide | 0.02 mol (1.30 cm$^3$) |
| Anhydrous dimethylformamide | 50 cm$^3$ |

Procedure:

0.01 mol of 3-methyl-6-(2-trifluoroacetamidoethyl)benzothiazolinone and 0.04 mol of potassium carbonate in 50 cm³ of anhydrous dimethylformamide are introduced into a ground-necked flask on which is fitted a water-condenser.

The mixture is left at reflux of the solvent with stirring for thirty minutes. 0.02 mol of methyl iodide is added.

After reaction for two hours at reflux of the dimethylformamide, the reaction mixture is cooled and is then poured into 100 cm³ of ice-water.

The precipitate formed is drained, washed with water, dried and then recrystallized.

| Molecular weight | 318.24 g.mol⁻¹ |
|---|---|
| Melting point | 122–123° C. |
| Yield | 91% |
| Recrystallization solvent | cyclohexane |

PREPARATION 8: 3-METHYL-6-[4-(N-METHYLTRIFLUOROACETAMIDO)BUTYL]BENZOTHIAZOLINONE

Reactants:

| 3-Methyl-6-(4-trifluoroacet-amidobutyl)benzothiazolinone | 0.01 mol (3.32 g) |
|---|---|
| Potassium carbonate | 0.04 mol (5.52 g) |
| Methyl iodide | 0.02 mol (1.25 cm³) |
| Anhydrous dimethylformamide | 50 cm³ |

Procedure:

The procedure is identical to that used to obtain the compound described in Preparation 7.

| Molecular weight | 346.30 g.mol⁻¹ |
|---|---|
| Melting point | 63–64° C. |
| Yield | 82% |
| Recrystallization solvent | cyclohexane |

PREPARATION 9: 3-METHYL-6-[2-(N-METHYLAMINO)ETHYL]BENZOTHIAZOLINONE HYDROCHLORIDE

Reactants:

| 3-Methyl-6-[2-(N-methyltrifluoro-acetamido)ethyl]benzothiazolinone | 0.01 mol (3.18 g) |
|---|---|
| Potassium carbonate | 0.04 mol (5.52 g) |
| Methanol/water mixture (6:1) | 70 cm³ |

Procedure:

Into a ground-necked flask on which is fitted a water-condenser and which contains 60 cm³ of methanol and 10 cm³ of water, is placed 0.01 mol of 3-methyl-6-[2-(N-methyltrifluoroacetamido)ethyl]benzothiazolinone.

0.04 mol of potassium carbonate is added. The mixture is maintained at reflux of the solvents for one hour. The methanol is evaporated off, 50 cm³ of water are added to the residue and this is extracted three times with 50 cm³ of ethyl acetate. The combined organic phases are dried over potassium carbonate and filtered, and the solvent is evaporated off.

The residue is dissolved in 50 cm³ of anhydrous acetone and is sparged with gaseous hydrogen chloride. The precipitate obtained is drained, dried and then recrystallized.

| Molecular weight: | 258.74 g.mol⁻¹ |
|---|---|
| Melting point: | 203–204° C. |
| Yield | 80% |
| Recrystallization solvent | anhydrous acetone |

PREPARATION 10: 3-METHYL-6-[4-(N-METHYLAMINO)BUTYL]BENZOTHIAZOLINONE HYDROCHLORIDE

Reactants:

| 3-Methyl-6-[4-(N-methyltrifluoroacetamido)-butyl]benzothiazolinone | 0.01 mol (3.46 g) |
|---|---|
| Potassium carbonate | 0.04 mol (5.52 g) |
| Methanol/water mixture (6:1) | 70 cm³ |

Procedure:

The procedure is identical to that used to obtain the compound described in Preparation 9.

| Molecular weight: | 286.75 g.mol⁻¹ |
|---|---|
| Melting point: | 130–132° C. |
| Yield | 80% |
| Recrystallization solvent | anhydrous acetone |

PREPARATION 11: 3-METHYL-6-{2-[N-(2-HYDROXYETHYL)-N-METHYLAMINO]ETHYL}BENZOTHIAZOLINONE

Reactants:

| 3-Methyl-6-(2-bromoethyl)-benzothiazolinone: | 0.032 mol (8.7 g) |
|---|---|
| 2-N-Methylethanolamine | 0.033 mol (2.6 cm³) |
| Triethylamine | 0.033 mol (4.6 cm³) |
| Anhydrous acetone | 60 cm³ |

Procedure:

0.033 mol of 2-N-methylethanolamine, 0.032 mol of 3-methyl-6-(2-bromoethyl) benzothiazolinone and 0.033 mol of triethylamine are introduced into a 250 cm³ ground-necked flask containing 60 cm³ of anhydrous acetone.

The reaction mixture is heated to reflux of the anhydrous acetone for 15 hours. It is allowed to cool and the solvent is then evaporated off on a water bath, under reduced pressure.

The evaporation residue is taken up in 30 cm³ of aqueous 2N hydrochloric acid solution. This is extracted with 30 cm³ of ethyl ether. The aqueous phase is basified with aqueous 10% sodium hydroxide solution and is extracted a further three times with 50 cm³ of chloroform. The chloroform fractions are combined, dried over calcium chloride, filtered and then evaporated on a water bath, under reduced pressure.

The residue is taken up in 50 cm³ of anhydrous ether and is sparged with gaseous hydrogen chloride, and the precipitate formed is drained and recrystallized.

| Molecular weight | 302.75 g.mol⁻¹ |
|---|---|

PREPARATION 12:
3-METHYL-6-{4-[N-(2-HYDROXYETHYL)-N-METHYLAMINO]BUTYL} BENZOTHIAZOLINONE

Reactants:

| | |
|---|---|
| 3-Methyl-6-(4-bromobutyl)-benzothiazolinone | 0.010 mol (3 g) |
| 2-N-Methylethanolamine | 0.012 mol (1 cm³) |
| Triethylamine | 0.012 mol (1.66 cm³) |
| Anhydrous acetone | 45 cm³ |

Procedure:

The procedure is identical to that used to produce the compound described in Preparation 11.

| | |
|---|---|
| Molecular weight | 330.81 g.mol⁻¹ |
| Yield | 75% |
| Melting point | 60° C. |
| Recrystallization solvent | acetone |

PREPARATION 13:
3-METHYL-6-{2-[N-(2-CHLOROETHYL)-N-METHYLAMINO]ETHYL} BENZOTHIAZOLINONE

Reactants:

| | |
|---|---|
| 3-Methyl-6-{2-[N-(2-hydroxy-ethyl)-N-methylamino]ethyl}benzothiazolinone hydrochloride | 0.011 mol (3.3 g) |
| Thionyl chloride | 0.044 mol (3.2 cm³) |
| Anhydrous chloroform | 100 cm³ |

Procedure:

0.011 mol of 3-methyl-6-{2-[N-(2-hydroxyethyl)-N-methylamino]ethyl} benzothiazolinone hydrochloride is dissolved in 100 cm³ of hot anhydrous chloroform contained in a 250 cm³ ground-necked round-bottomed flask, 0.044 mol of thionyl chloride is added dropwise and the reaction mixture is heated at reflux for 1 hour.

The chloroform-thionyl chloride mixture is evaporated off on a water bath, under reduced pressure.

The residue is taken up in 50 cm³ of anhydrous ether, triturated and left stirring for 30 minutes. The precipitate obtained is drained and recrystallized.

| | |
|---|---|
| Molecular weight | 321.19 g.mol⁻¹ |
| Yield: | 90% |
| Melting point | 144–147° C. |
| Recrystallization solvent | acetone |

PREPARATION 14:
3-METHYL-6-{4-[N-(2-CHLOROETHYL)-N-METHYLAMINO]BUTYL} BENZOTHIAZOLINONE

Reactants:

| | |
|---|---|
| 3-Methyl-6-{2-[N-(4-hydroxy-ethyl)-N-methylamino]butyl}benzothiazolinone hydrochloride | 0.008 mol (2.6 g) |
| Thionyl chloride | 0.033 mol (2.6 cm³) |
| Anhydrous chloroform | 100 cm³ |

Procedure:

The procedure is identical to that used to obtain the compound described in Preparation 13.

| | |
|---|---|
| Molecular weight | 349.25 g.mol⁻¹ |
| Yield | 88% |
| Melting point | 176–179° C. |
| Recrystallization solvent | acetone |

PREPARATION 15:
3-METHYL-6-{2-[N-(2-IODOETHYL)-N-METHYLAMINO]ETHYL} BENZOTHIAZOLINONE

Reactants:

| | |
|---|---|
| 3-Methyl-6-{2-[N-(2-chloro-ethyl)-N-methylamino]ethyl}-benzothiazolinone hydrochloride | 0.0068 mol (2.2 g) |
| Potassium iodide | 0.027 mol (4.5 g) |
| Anhydrous acetone | 50 cm³ |

Procedure:

0.0068 mol of 3-methyl-6-{2-[N-(2-chloroethyl)-N-methylamino]ethyl}benzothiazolinone hydrochloride and 0.027 mol of potassium iodide are introduced into a 250 cm³ ground-necked flask containing 50 cm³ of anhydrous acetone.

The mixture is heated at reflux of the acetone for 24 hours. It is allowed to cool and filtered, and the filtrate is then evaporated on a water bath, under reduced pressure.

The residue is taken up in anhydrous ether and is sparged with gaseous hydrogen chloride, then the precipitate obtained is drained and recrystallized.

| | |
|---|---|
| Molecular weight | 412.75 g.mol⁻¹ |
| Yield: | 90% |
| Melting point | 124–126° C. |

PREPARATION 16:
3-METHYL-6-{4-[N-(2-IODOETHYL)-N-METHYLAMINO]BUTYL} BENZOTHIAZOLINONE

Reactants:

| | |
|---|---|
| 3-Methyl-6-{4-[N-(2-chloro-ethyl)-N-methylamino]butyl}benzothiazolinone hydrochloride | 0.011 mol (4 g) |
| Potassium carbonate | 0.044 mol (7.3 g) |

—continued

| | |
|---|---|
| Yield | 80% |
| Melting point | 55° C. |
| Recrystallization solvent | acetone |

-continued

| Anhydrous acetone | 60 cm³ |

Procedure:

The procedure is identical to that used to obtain the compound described in Preparation 15.

| Molecular weight | 440.79 g.mol¹ |
| Yield | 88% |
| Melting point | 130–132° C. |

EXAMPLE 1:
3-METHYL-6-[2-(4-BENZYLPIPERID-1-YL) ETHYL]BENZOTHIAZOLINONE

Procedure:

0.0073 mol (2.00 g) of 3-methyl-6-(2-bromoethyl)benzothiazolinone described in Application EP 478,446, 0.0073 mol (1.30 cm³) of 4-benzylpiperidine and 0.0073 mol (1.00 cm³) of triethylamine are introduced into a 250 cm³ ground-necked flask fitted with a condenser and containing 70 cm³ of anhydrous acetone.

The mixture is heated at reflux of the acetone for 30 hours. The triethylamine hydrobromide precipitate is drained off and the filtrate is then evaporated on a water bath, under reduced pressure. The residue is taken up in aqueous 1N hydrochloric acid solution and is extracted with ether.

The aqueous phase is basified with 10% sodium hydroxide solution. This is extracted twice with ether and the ether phases are combined, dried over calcium chloride, filtered and evaporated under reduced pressure.

The residue is taken up in anhydrous ether and sparged with gaseous hydrogen chloride, and the precipitate formed is drained and recrystallized.

Molecular weight: 402.91 g mol⁻¹ for $C_{22}H_{27}ClN_2OS$

Yield: 56%

Melting point (hydrochloride): 157°–159° C.

Recrystallization solvent: acetone

Elemental analysis:

|  | % C | % H | % N |
| --- | --- | --- | --- |
| Calculated | 65.58 | 6.75 | 6.95 |
| Found | 65.74 | 6.95 | 6.95 |

Infrared spectrometry:

| 3400–2500 | cm⁻¹ | ν NH⁺ (hydrochloride) |
| 2960 | cm⁻¹ | ν CH (alkyls) |
| 1680 | cm⁻¹ | ν CO (NCOS) |
| 1590 | cm⁻¹ | ν C=C (aromatics) |

Nuclear magnetic resonance spectrometry (80 MHz; DMSO-d6):

| δ = 1.40–1.80 | ppm | (multiplet, 4H) | (ethyl) |
| δ = 3.20 | ppm | (singlet, 2H) | $CH_2$—$C_6H_5$ |
| δ = 7.00–7.50 | ppm | (multiplet, 8H) | aromatic H |
| δ = 9.00 | ppm | (peak, 1 H) | NH⁺ exchangeable in $D_2O$ |

EXAMPLE 2:
3-METHYL-6-[4-(4-BENZYLPIPERID-1-YL) BUTYL]BENZOTHIAZOLINONE

Reactants:

| 3-Methyl-6-(4-bromobutyl) benzothiazolinone | 0.005 mol (1.40 g) |
| 4-Benzylpiperidine | 0.005 mol (0.90 cm³) |
| Potassium carbonate | 0.010 mol (1.40 g) |
| Anhydrous dimethylformamide | 60 cm³ |

Procedure:

The procedure is identical to that used in Example 1, replacing 3-methyl-6-(2-bromoethyl)benzothiazolinone by 3-methyl-6-(4-bromobutyl)benzothiazolinone described in Application EP 478,446 and replacing triethylamine/acetone by potassium carbonate/dimethylformamide.

| Molecular weight | 430.98 g.mol⁻¹ for $C_{24}H_{31}ClN_2OS$ |
| Yield | 50% |
| Melting point (hydrochloride) | 160–162° C. |
| Recrystallization solvent | acetone-ether (2/3) |

Elemental analysis:

|  | % C | % H | % N |
| --- | --- | --- | --- |
| Calculated | 66.88 | 7.25 | 6.50 |
| Found | 67.02 | 6.98 | 6.30 |

Infrared spectrometry:

| 3400–2440 | cm⁻¹ | ν NH⁺ (hydrochloride) |
| 3020–2860 | cm⁻¹ | ν CH (alkyls) |
| 1650 | cm⁻¹ | ν CO (NCOS) |
| 1600 | cm⁻¹ | ν C=C (aromatics) |

Nuclear magnetic resonance spectrometry (80 MHz; DMSO-d₆):

| δ = 6.80–7.40 | ppm | (multiplet, 8H) | aromatic H |
| δ = 12.00 | ppm | (peak, 1H) | NH⁺ exchangeable in $D_2O$ |

EXAMPLE 3:
3-METHYL-6-[2-(4-PHENYLPIPERID-1-YL) ETHYL]BENZOTHIAZOLINONE

Reactants:

| 3-Methyl-6-(2-bromoethyl)- benzothiazolinone | 0.0055 mol (1.5 g) |
| 4-Phenylpipeddine | 0.0055 mol (0.88 g) |
| Triethylamine | 0.0055 mol (0.80 cm³) |
| Anhydrous acetone | 40 cm³ |

Procedure:

The procedure is identical to that used in Example 1, replacing 4-benzylpiperidine by 4-phenylpiperidine.

| Molecular weight | 388.80 g.mol⁻¹ for $C_{21}H_{25}ClN_2OS$ |
| Yield | 60% |
| Melting point | 260–261 ° C. |

-continued

| (hydrochloride) | |
|---|---|
| Recrystallization solvent | absolute alcohol |

Elemental analysis: for $C_{21}H_{25}ClN_2OS$; 1.25 $H_2O$, MW=411.32 g.mol$^{-1}$

| | % C | % H | % N |
|---|---|---|---|
| Calculated | 61.31 | 6.12 | 6.81 |
| Found | 61.16 | 6.16 | 6.73 |

Infrared spectrometry:

| 3000–2880 | cm$^{-1}$ | ν CH (alkyls) |
|---|---|---|
| 2500 | cm$^{-1}$ | ν NH$^+$ (hydrochloride) |
| 1680 | cm$^{-1}$ | ν CO (NCOS) |
| 1600–1570 | cm$^{-1}$ | ν C=C (aromatics) |

Nuclear magnetic resonance spectrometry (80 MHz; DMSO-d$_6$):

| $\delta$ = 1.60–2.20 | ppm | (multiplet, 4H) | (ethyl) |
|---|---|---|---|
| $\delta$ = 3.00–3.80 | ppm | (multiplet, 12H) | NCH$_3$ and piperidine |
| $\delta$ = 7.10–7.70 | ppm | (multiplet, 8H) | aromatic H |
| $\delta$ = 10.50 | ppm | (peak, 1 H) | NH$^+$ exchangeable in D$_2$O |

EXAMPLE 4:
3-METHYL-6-[4-(4-PHENYLPIPERID-1-YL)BUTYL]BENZOTHIAZOLINONE

Reactants:

| 3-Methyl-6-(4-bromobutyl)-benzothiazolinone | 0.0073 mol (2.00 g) |
|---|---|
| 4-Phenylpiperidine | 0.0073 mol (1.20 cm$^3$) |
| Triethylamine | 0.0073 mol (1.00 cm$^3$) |
| Anhydrous acetone | 70 cm$^3$ |

Procedure:

The procedure is identical to that used in Example 2, replacing 4-benzylpiperidine by 4-phenylpiperidine.

| Molecular weight | 416.93 g.mol$^{-1}$ for $C_{23}H_{29}ClN_2OS$ |
|---|---|
| Yield | 43% |
| Melting point (hydrochloride) | 210–212° C. |
| Recrystallization solvent | absolute alcohol |

Elemental analysis: for $C_{23}H_{29}ClN_2OS$; 0.5 $H_2O$, MW=425.94 g.mol$^{-1}$

| | % C | % H | % N |
|---|---|---|---|
| Calculée | 64.85 | 6.86 | 6.57 |
| Trouvée | 64.99 | 7.10 | 6.64 |

Infrared spectrometry:

| 3020–2840 | cm$^{-1}$ | ν CH (alkyls) |
|---|---|---|
| 2500 | cm$^{-1}$ | ν NH$^+$ (hydrochloride) |
| 1670 | cm$^{-1}$ | ν CO (NCOS) |
| 1590 | cm$^{-1}$ | ν C=C (aromatics) |

Nuclear magnetic resonance spectrometry (300 MHz; DMSO-d$_6$):

| $\delta$ = 1.50–1.80 | ppm | (massif, 4H) | CH$_2$—CH$_2$—CH$_2$—CH$_2$ |
|---|---|---|---|
| $\delta$ = 3.40 | ppm | (singulet, 3H) | NCH$_3$ |
| $\delta$ = 7.20–7.70 | ppm | (massif, 8H) | H aromatiques |
| $\delta$ = 10.50 | ppm | (signal, 1H) | NH$^+$ exchangeable in D$_2$O |

EXAMPLES 5 TO 8

By working in the same manner as in Examples 1 to 4, but replacing 3-methyl-6-(2-bromoethyl)benzothiazolinone and 3-methyl-6-(4-bromobutyl)benzothiazolinone by 3-methyl-6-(2-bromoethyl)benzoxazolinone and 3-methyl-6-(4-bromobutyl)benzoxazolinone described in Patent EP 506,539, the products of the following examples are respectively obtained:

EXAMPLE 5:
3-METHYL-6-[2-(4-BENZYLPIPERID-1-YL)ETHYL]BENZOXAZOLINONE

EXAMPLE 6:
3-METHYL-6-[4-(4-BENZYLPIPERID-1-YL)BUTYL]BENZOXAZOLINONE

EXAMPLE 7:
3-METHYL-6-[2-(4-PHENYLPIPERID-1-YL)ETHYL]BENZOXAZOLINONE

EXAMPLE 8:
3-METHYL-6-[4-(4-PHENYLPIPERID-1-YL)BUTYL]BENZOXAZOLINONE

EXAMPLE 9:
3-METHYL-6-{2-[4-(4-FLUOROBENZYL)PIPERID-1-YL]ETHYL}BENZOTHIAZOLINONE

By working as in Example 1, but replacing 4-benzylpiperidine by 4-(4-fluorobenzyl)piperidine, the title compound is obtained.

EXAMPLE 10: 3-METHYL-6-{2-[4-(4-FLUOROBENZYL)PIPERID-1-YL]ETHYL}BENZOXAZOLINONE

By working in the same manner as in Example 9, but replacing 3-methyl-6-(2-bromoethyl)benzothiazolinone by 3-methyl-6-(2-bromoethyl)benzoxazolinone, the title compound is obtained.

EXAMPLE 11:
3-METHYL-6-{2-[N-(2-PYRROLIDIN-1-YL-ETHYL)-N-METHYLAMINO]ETHYL}BENZOTHIAZOLINONE

Reactants:

| 3-Methyl-6-{2-[N-(2-iodoethyl)-N-methylamino]ethyl}benzothiazolinone hydrochloride (Preparation 15) | 0.0041 mol (1.73 g) |
|---|---|
| Pyrrolidine | 0.0041 mol (0.40 cm$^3$) |
| Triethylamine | 0.0082 mol (1.20 cm$^3$) |

-continued

| Anhydrous acetone | 50 cm³ |

Procedure:

The procedure is identical to that used in Example 1, replacing, on the one hand, 4-benzylpiperidine by pyrrolidine and, on the other hand, 3-methyl-6-(2-bromoethyl)benzothiazolinone by 3-methyl-6-{2-[N-(2-iodoethyl)-N-methylamino)ethyl} benzothiazolinone hydrochloride.

| Molecular weight | 392.32 g/mol$^{-1}$ for $C_{17}H_{27}Cl_2N_3OS$ |
| Yield | 50% |
| Melting point (dihydrochloride) | 250–252° C. |
| Recrystallization solvent | absolute alcohol |

Elemental analysis:

|  | % C | % H | % N |
| --- | --- | --- | --- |
| Calculated | 52.04 | 6.94 | 10.71 |
| Found | 51.78 | 7.00 | 10.61 |

Infrared spectrometry:

| 3400–2500 | cm$^{-1}$ | ν NH$^+$ (hydrochloride) |
| 3000–2800 | cm$^{-1}$ | ν CH (alkyls) |
| 1670 | cm$^{-1}$ | ν CO (NCOS) |
| 1600 | cm$^{-1}$ | ν C=C (aromatics) |

Nuclear magnetic resonance spectrometry (300 MHz; DMSO-d$_6$):

| δ = 2.90 | ppm | (singlet, 3H) | NCH$_3$ (amine) |
| δ = 3.40 | ppm | (singlet, 3H) | NCH$_3$ (thiocarbamate) |
| δ = 7.30–7.40 | ppm | (multiplet, 2H) | H$_{4,5}$ (benzothiazolinone) |
| δ = 7.60 | ppm | (singlet, 1H) | H$_7$ (benzothiazolinone) |
| δ = 10.10 | ppm | (peak, 2H) | 2NH$_2^+$ exchangeable in D$_2$O |

EXAMPLE 12:
3-METHYL-6-{2-[N-(2-PIPERID-1-YL-ETHYL)-N-METHYLAMINO]ETHYL} BENZOTHIAZOLINONE

Procedure:

0.0041 mol (1.08 g) of 3-methyl-6-[2-(N-methylamino)ethyl]benzothiazolinone (Preparation 9), 0.0041 mol (0.75 g) of 1-(2-chloroethyl)piperidine hydrochloride and 0.0082 mol (1.20 cm³) of triethylamine are introduced into a 250 cm³ ground-necked flask containing 50 cm³ of anhydrous acetone.

The reaction mixture is heated at reflux for 48 hours. It is filtered and the acetone is evaporated off on a water bath, under reduced pressure. The residue is taken up in 50 cm³ of aqueous acetic acid solution and is extracted three times with 40 cm³ of chloroform.

The aqueous phase is basified with 10% potassium bicarbonate solution. This is extracted three times with 50 cm³ of chloroform. The combined chloroform phases are dried over calcium chloride, filtered and then evaporated on a water bath, under reduced pressure.

The residue is taken up in 30 cm³ of anhydrous ether and sparged with gaseous hydrogen chloride, and the precipitate formed is drained and recrystallized.

| Molecular weight | 406.35 g.mol$^{-1}$ for $C_{18}H_{29}Cl_2N_3OS$ |
| Yield | 50% |
| Melting point (dihydrochloride) | >260° C. |
| Recrystallization solvent | absolute alcohol |

Elemental analysis:

|  | % C | % H | % N |
| --- | --- | --- | --- |
| Calculated | 53.20 | 7.19 | 10.34 |
| Found | 53.02 | 7.02 | 10.52 |

Infrared spectrometry:

| 3400–2500 | cm$^{-1}$ | ν NH$^+$ (hydrochloride) |
| 3000–2800 | cm$^{-1}$ | ν CH (alkyls) |
| 1670 | cm$^{-1}$ | ν CO (NCOS) |
| 1600 | cm$^{-1}$ | ν C=C (aromatics) |

Nuclear magnetic resonance spectrometry (80 MHz; DMSO-d$_6$):

| δ = 2.80 | ppm | (singlet, 3H) | NCH$_3$ (amine) |
| δ = 7.30–7.40 | ppm | (multiplet, 2H) | H$_{4,5}$ (benzothiazolinone) |
| δ = 7.60 | ppm | (multiplet, 1H) | H$_7$ (benzothiazolinone) |
| δ = 10.8–11.10 | ppm | (peak, 2H) | 2NH$^+$ exchangeable in D$_2$O |

EXAMPLE 13:
3-METHYL-6-{2-[N-(2-PERHYDRAZEPIN-1-YL-ETHYL)-N-METHYLAMINO]ETHYL} BENZOTHIAZOLINONE

Reactants:

| 3-Methyl-6-[2-(N-methylamino)ethyl]benzothiazolinone | 0.0042 mol (1.1 g) |
| 1-(2-Chloroethyl)perhydroazepine hydrochloride | 0.0042 mol (0.9 g) |
| Triethylamine | 0.0042 mol (0.6 cm³) |
| Anhydrous acetone | 50 cm³ |

Procedure:

The procedure is identical to that used in Example 12, replacing 1-(2-chloroethyl)piperidine by 1-(2-chloroethyl)perhydroazepine.

| Molecular weight | 420.37 g.mol$^{-1}$ for $C_{19}H_{31}Cl_2N_3OS$ |
| Yield | 30% |
| Melting point (dihydrochloride) | 262–264° C. |
| Recrystallization solvent | acetone-ether (2/3) |

Elemental analysis:

|  | % C | % H | % N |
| --- | --- | --- | --- |
| Calculated | 54.28 | 7.32 | 9.99 |
| Found | 54.38 | 7.16 | 9.70 |

Infrared spectrometry:

| | | |
|---|---|---|
| 2920 | cm$^{-1}$ | ν CH (alkyls) |
| 2600–2300 | cm$^{-1}$ | ν NH$^+$ (hydrochloride) |
| 1670 | cm$^{-1}$ | ν CO (NCOS) |
| 1600 | cm$^{-1}$ | ν C=C (aromatics) |

Nuclear magnetic resonance spectrometry (80 MHz; DMSO-d$_6$):

| | | | |
|---|---|---|---|
| δ = 2.90 | ppm | (singlet, 3H) | NCH$_3$ (amine) |
| δ = 7.20–7.50 | ppm | (multiplet, 2H) | H$_{4,5}$ (benzothiazolinone) |
| δ = 7.80 | ppm | (singlet, 1H) | H$_7$ (benzothiazolinone) |
| δ = 11.30 | ppm | (peak, 2H) | 2NH$^+$ exchangeable in D$_2$O |

EXAMPLE 14:
3-METHYL-6-{4-[N-(2-PYRROLIDIN-1-YL-ETHYL)-N-METHYLAMINO]BUTYL} BENZOTHIAZOLINONE

Reactants:

| | |
|---|---|
| 3-Methyl-6-{4-[N-(2-iodoethyl)-N-methylamino]butyl}benzothiazolinone hydrochloride | 0.0074 mol (1.50 g) |
| Pyrrolidone | 0.0074 mol (0.62 cm$^3$) |
| Triethylamine | 0.0150 mol (2.00 cm$^3$) |
| Anhydrous acetone | 50 cm$^3$ |

Procedure:

The procedure is identical to that used in Example 1, but replacing 4-benzylpiperidine by pyrrolidine and 3-methyl-6-(2-bromoethyl)benzothiazolinone by 3-methyl-6-{4-[N-(2-iodoethyl)-N-methylamino]butyl}benzothiazolinone hydrochloride (Preparation 16).

| | |
|---|---|
| Molecular weight | 420.37 g.mol$^{-1}$ for C$_{19}$H$_{31}$Cl$_2$N$_3$OS |
| Yield | 55% |
| Melting point (dihydrochloride) | 244–246° C. |
| Recrystallization solvent | absolute alcohol |

Elemental analysis:

| | % C | % H | % N |
|---|---|---|---|
| Calculated | 54.23 | 7.13 | 9.99 |
| Found | 54.13 | 7.20 | 10.14 |

Infrared spectrometry:

| | | |
|---|---|---|
| 3400–2400 | cm$^{-1}$ | ν NH$^+$ (hydrochloride) |
| 2900 | cm$^{-1}$ | ν CH (alkyls) |
| 1670 | cm$^{-1}$ | ν CO (NCOS) |
| 1600 | cm$^{-1}$ | ν C=C (aromatics) |

Nuclear magnetic resonance spectrometry (80 MHz; DMSO-d$_6$):

| | | | |
|---|---|---|---|
| δ = 2,70 | ppm | (multiplet, 2H) | (benzothiazolinone-CH$_2$) |
| δ = 2,90 | ppm | (singulet, 3H) | NCH$_3$ (amine) |
| δ = 3,00–3,30 | ppm | (massif, 4H) | CH$_2$—N(CH$_3$)—CH$_2$ |
| δ = 7,20–7,30 | ppm | (massif, 2H) | H$_{4,5}$ (benzothiazolinone) |
| δ = 7,60 | ppm | (singulet, 1H) | H$_7$ (benzothiazolinone) |
| δ = 10.90 | ppm | (peak, 1H) | NH$^+$ exchangeable in D$_2$O |
| δ = 11.20 | ppm | (peak, 1H) | NH$^+$ exchangeable in D$_2$O |

EXAMPLE 15:
3-METHYL-6-{4-[N-(2-PIPERID-1-YL-ETHYL)-N-METHYLAMINO]BUTYL} BENZOTHIAZOLINONE

Reactants:

| | |
|---|---|
| 3-Methyl-6-[4-(N-methylamino)-butyl]benzothiazolinone (Preparation 10) | 0.0037 mol (1.5 g) |
| 1-(2-Chloroethyl)piperidine hydrochloride | 0.0037 mol (0.36 cm$^3$) |
| Triethylamine | 0.0037 mol (0.52 cm$^3$) |
| Anhydrous acetone | 50 cm$^3$ |

Procedure:

The procedure is identical to that used in Example 1, replacing 4-benzylpiperidine by 1-(2-chloroethyl)piperidine hydrochloride and 3-methyl-6-(2-bromoethyl)benzothiazolinone by 3-methyl-6-[4-(N-methylamino)butyl]benzothiazolinone (Preparation 10).

| | |
|---|---|
| Molecular weight | 422.37 g.mol$^{-1}$ for C$_{20}$H$_{33}$Cl$_2$N$_3$OS |
| Yield | 55% |
| Melting point (dihydrochloride) | 252–254° C. |
| Recrystallization solvent | absolute alcohol |

Elemental analysis:

| | % C | % H | % N |
|---|---|---|---|
| Calculated | 54.02 | 7.87 | 9.94 |
| Found | 54.37 | 7.71 | 9.56 |

Infrared spectrometry:

| | | |
|---|---|---|
| 3400–2480 | cm$^{-1}$ | ν NH$^+$ (hydrochloride) |
| 2990 | cm$^{-1}$ | ν CH (alkyls) |
| 1670 | cm$^{-1}$ | ν CO (NCOS) |
| 1600 | cm$^{-1}$ | ν C=C (aromatics) |

Nuclear magnetic resonance spectrometry: (300 MHz; DMSO-d$_6$):

| | | | |
|---|---|---|---|
| δ = 2.60–2.90 | ppm | (massif, 7H) | CH$_2$—N(CH$_3$)—CH$_2$ |
| δ = 7.20–7.30 | ppm | (massif, 2H) | H$_{4,5}$ (benzothiazolinone) |
| δ = 7.50 | ppm | (singulet, 1H) | H$_7$ (benzothiazolinone) |
| δ = 10.70 | ppm | (signal, 2H) | 2NH$^+$ exchangeable in D$_2$O |

EXAMPLE 16: 3-METHYL-6-{ 4-[N-(2-PERHYDROAZEPIN-1-YL-ETHYL)-N-METHYLAMINO]BUTYL} BENZOTHIAZOLINONE

Reactants:

| | |
|---|---|
| 3-Methyl-6-[4-(N-methylamino)-butyl]benzothiazolinone | 0.0042 mol (1.10 g) |
| 1-(2-Chloroethyl)perhydroazepine hydrochloride | 0.0084 mol (1.80 g) |

-continued

| Triethylamine | 0.0084 mol (1.20 cm³) |
| Anhydrous acetone | 50 cm³ |

Procedure:

The procedure is identical to that used in Example 12, but replacing 3-methyl-6-[2-(N-methylamino)ethyl]benzothiazolinone by 3-methyl-6-[4-(N-methylamino)butyl]benzothiazolinone and 1-(2-chloroethyl)piperidine by 1-(2-chloroethyl)perhydroazepine.

| Molecular weight | 448.43 g.mol$^{-1}$ for $C_{21}H_{35}Cl_2N_3OS$ |
| Yield | 45% |
| Melting point (dihydrochloride) | 232–234° C. |
| Recrystallization solvent | acetone-ether (2/3) |

Elemental analysis: for $C_{21}H_{35}Cl_2N_3OS$; 0.75 $H_2O$, MW=461.94 g/mol$^{-1}$

|  | % C | % H | % N |
| --- | --- | --- | --- |
| Calculated | 54.59 | 7.80 | 9.09 |
| Found | 54.71 | 7.42 | 9.05 |

Infrared spectrometry:

| 2600–2300 | cm$^{-1}$ | ν NH$^+$ (hydrochloride) |
| 2920 | cm$^{-1}$ | ν CH (alkyls) |
| 1670 | cm$^{-1}$ | ν CO (NCOS) |
| 1600 | cm$^{-1}$ | ν C=C (aromatics) |

Nuclear magnetic resonance spectrometry: (80 MHz; DMSO-d$_6$):

| δ = 3.50–3.60 | ppm | (multiplet, 4H) | CH$_2$—N(CH$_3$)—CH$_2$ |
| δ = 7.20–7.30 | ppm | (multiplet, 2H) | H$_{4,5}$ (benzothiazolinone) |
| δ = 7.60 | ppm | (singlet, 1H) | H$_7$ (benzothiazolinone) |
| δ = 10.90 | ppm | (peak, 2H) | 2NH$^+$ exchangeable in D$_2$O |

EXAMPLE 17: 3-METHYL-6-{4-[N-(CYCLOPROPYLAMINOETHYL)-N-METHYLAMINO]BUTYL} BENZOTHIAZOLINONE

By working as in Example 14, but replacing pyrrolidine by cyclopropylamine, the title product is obtained.

EXAMPLE 18: 3-METHYL-6-{4-[N-(CYCLOHEXYLAMINOETHYL)-N-METHYLAMINO]BUTYL} BENZOTHIAZOLINONE

By working as in Example 14, but replacing pyrrolidine by cyclohexylamine, the title product is obtained.

EXAMPLE 19: 3-METHYL-6-{4-[N-(n,n-DIPROPYLAMINOETHYL)-N-METHYLAMINO]BUTYL}BENZOTHIAZOLINONE

By working as in Example 14, but replacing pyrrolidine by di-n-propylamine, the title product is obtained.

EXAMPLES 20 TO 30:

By working as in Examples 1 to 19, but using the benzothiazolinone or benzoxazolinone compounds which are not methylated in the 3-position, the compounds of the following examples are obtained:

EXAMPLE 20:
6-[2-(4-BENZYLPIPERID-1-YL)ETHYL] BENZOTHIAZOLINONE

EXAMPLE 21:
6-[4-(4-BENZYLPIPERID-1-YL)BUTYL] BENZOTHIAZOLINONE

EXAMPLE 22:
6-[2-(4-PHENYLPIPERID-1-YL)ETHYL] BENZOTHIAZOLINONE

EXAMPLE 23:
6-[4-(4-PHENYLPIPERID-1-YL)BUTYL] BENZOTHIAZOLINONE

EXAMPLE 24:
6-[2-(4-BENZYLPIPERID-1-YL)ETHYL] BENZOXAZOLINONE

EXAMPLE 25:
6-[4-(4-BENZYLPIPERID-1-YL)BUTYL] BENZOXAZOLINONE

EXAMPLE 26:
6-[2-(4-PHENYLPIPERID-1-YL)ETHYL] BENZOXAZOLINONE

EXAMPLE 27:
6-[4-(4-PHENYLPIPERID-1-YL)BUTYL] BENZOXAZOLINONE

EXAMPLE 28:
6-{2-[4-(4-FLUOROBENZYL)PIPERID-1-YL] ETHYL}BENZOTHIAZOLINONE

EXAMPLE 29:
6-{2-[4-(4-FLUOROBENZYL)PIPERID-1-YL] ETHYL}BENZOXAZOLINONE

EXAMPLE 30: 6-{2-[N-(2-PYRROLIDIN-1-YLETHYL)-N-METHYLAMINO]ETHYL}BENZOTHIAZOLINONE

EXAMPLE 31: 6-{2-[N-(2-PIPERID-1-YLETHYL)-N-METHYLAMINO]ETHYL}BENZOTHIAZOLINONE

EXAMPLE 32: 6-{2-[N-(2-PERHYDROAZEPIN-1-YLETHYL)-N-METHYLAMINO]ETHYL}BENZOTHIAZOLINONE

EXAMPLE 33: 6-{4-[N-(2-PYRROLIDIN-1-YLETHYL)-N-METHYLAMINO]BUTYL}BENZOTHIAZOLINONE

EXAMPLE 34: 6-{4-[N-(2-PIPERID-1-YLETHYL)-N-METHYLAMINO]BUTYL}BENZOTHIAZOLINONE

EXAMPLE 35: 6-{4-[N-(2-PERHYDROAZEPIN-1-YLETHYL)-N-METHYLAMINO]BUTYL}BENZOTHIAZOLINONE

EXAMPLE 36: 6-{4-[N-(CYCLOPROPYLAMINOETHYL)-N-METHYLAMINO]BUTYL}BENZOTHIAZOLINONE

EXAMPLE 37: 6-{4-[N-(CYCLOHEXYLAMINOETHYL)-N-METHYLAMINO]BUTYL}BENZOTHIAZOLINONE

EXAMPLE 38: 6-{4-[N-(N,N-DI-n-PROPYLAMINOETHYL)-N-METHYLAMINO]BUTYL}BENZOTHIAZOLINONE

PHARMACOLOGICAL STUDY OF THE DERIVATIVES OF THE INVENTION

EXAMPLE A: STUDY OF THE ACUTE TOXICITY

The acute toxicity was evaluated after oral administration of a dose of 100 mg.kg$^{-1}$ of the compounds of the invention to batches of 8 mice (26±2 grams). The animals were observed at regular intervals during the first day and daily for the two weeks following the treatment.

It appears that the compounds of the invention are totally non-toxic. They cause no death after administration at a dose of 100 mg.kg$^{-1}$ and no disorders are observed after administration of this dose.

EXAMPLE B: IN VITRO RECEPTOR AFFINITY ANALYSIS

The products are tested on each receptor at 5 different concentrations ($10^{-5}$M, $10^{-6}$M, $10^{-7}$M, $10^{-8}$M, $10^{-9}$M) in triplicate. When the binding coefficient IC$_{50}$ is below a concentration of $10^{-6}$M, the Ki is measured using 12 concentrations of the product.

The table below features the receptors whose affinity for the compounds of the invention was determined, the tissue chosen, the concentration selected in order to determine the non-specific binding and the radioligand used to label the receptor.

| Receptor or site | Radioligand | Non-spécific binding | Tissue |
|---|---|---|---|
| 5-HT$_{1A}$ | 8-OH DPAT | $10^{-5}$M Buspirone | bovine hippocampus + frontal cortex |
| 5-HT$_{1B}$ | [$^3$H] Cyanopindolol or 5 OH Tryptamine | 1e$^{-5}$M cold sérotonin or propanolol | rat brain (frontal cortex + striatum) |
| 5-HT$_{1C}$ | N-methyl mesulergine | $10^{-5}$M Mianserin | pig chroroid plexus |
| 5-HT$_2$ | [$^3$H] kétanserine | $10^{-5}$M Spiperone | bovin frontal cortex |
| 5-HT$_3$ | [$^3$H] Quipazine or BRL 43694 | $10^{-5}$M ICS 255930 | NG 108-15 cells |
| α$_1$ | [$^3$H] Prazosin | $10^{-5}$M Phentolamine | rat brain |
| α$_2$ | [$^3$H] Rauwolfine | $10^{-5}$M Yohimbine | rat brain |
| D$_1$ | [$^3$H] SCH 23390 | $10^{-6}$M Butaclamol | bovine striatum |
| D$_2$ | [$^3$H] Raclopride | $10^{-6}$M Haloperidol ($10^{-5}$M spiperone) | bovine striatum |
| M1 | [$^3$H] Telenzepine | $10^{-5}$M Atropine | rat brain |
| H$_1$ | [$^3$H] Pyrilamine | $10^{-6}$M Chlorpheniramine | calf brain |
| σ (sigma) | [$^3$H] DTG | $10^{-6}$M 3-PPP | calf Hippocampus |

The results of the test showed that the compounds of the invention are powerful and selective ligands for the sigma receptors. By way of comparison, the compounds of the present invention have an affinity which is 100 times stronger than that of the compounds of Application EP 478,446 for the sigma receptor.

Moreover, the compounds of the present invention are also much more selective than the compounds of Application EP 478,446. In particular, they have 100 to 1000 times less affinity for the $D_2$ receptors than do the compounds of Application EP 478,446.

EXAMPLE C: ANTAGONISM OF THE HYPERMOTILITY INDUCED BY AMPHETAMINE 4 mg kg$^{-1}$ of d-amphetamine are injected intraperitoneally (IP) into groups of 10 NMRI-CERJ mice immediately after IP injection of the compound to be tested, and the mice are placed in an actimeter for 30 minutes.

The number of interruptions of the photoelectric cells is counted, as is the stereotyped behavior.

The activity of the compounds tested is expressed as a percentage of the antagonism of the hyperactivity induced by amphetamine.

The example which follows shows that the compounds of the invention are powerful antagonists of the hypermotility induced by amphetamine, which makes it possible to arrive at an activity in disorders of the central nervous system for the products of the invention.

| PRODUCT | Dose (mg.kg$^{-1}$) IP | | |
|---|---|---|---|
| | 2 | 4 | 8 |
| 3-methyl 6-[2-(4-benzylpiperidin-1-yl)ethyl]benzothiazolinone Exemple 1 | 23% | 50% | 63% |

EXAMPLE D: INVESTIGATION INTO THE CATALEPSIGENIC EFFECT

The catalepsigenic effect is investigated in rats via the intraperitoneal route. This test predicts the existence of side effects of extrapyramidal types. 6 groups of Wistar rats received an injection of the compounds of the invention and were then tested for their catalepsigenic activity after a 30-minute interval. Haloperidol is used as the reference.

The results which follow are expressed as a percentage of the maximum score possible.

The results show that the compounds of the invention have no catalepsigenic power when compared with haloperidol, which produces, at a dose of 2 mg.kg$^{-1}$, a catalepsigenic effect of 95% under the same study conditions. This result confirms the absence of side effects of extrapyramidal type for the products of the invention, which could be deduced from the receptor binding results (Example B).

EXAMPLE E: STUDY OF THE ANTIDEPRESSANT ACTIVITY OF THE COMPOUNDS OF THE INVENTION

PRINCIPLE:

The product study is based on the "acquired refusal" model which consists in inducing in the animal, by means of a series of uncontrollable aversive events, a deficit during subsequent avoidance tasks.

PROTOCOL:

This test was developed by Sherman A. D., Sacquitne J. L., and Petty F. (Pharmacol. Biochem. Behav., 1982, 16, 449–454). We use male Wistar rats weighing between 180 and 200 grams. The animals are kept in the animal house one week before the test, in plastic boxes, in groups of 10, at an ambient temperature of 21° C.± 1° C., with free access to water and food.

The animals are then isolated in small boxes and are subjected to 60 unavoidable electric shocks (0.8 mA every minute± 15 seconds). A control group of rats receives no electric shocks.

The avoidance learning capacity of the animals (passage from one compartment to the other in order to avoid the electric shocks) is evaluated 48 hours later and for 3 consecutive days. During the learning sessions, the animals undergo 2 tests per minute for 15 minutes. The number of avoidance failures is noted for each rat. The animals are treated (i.p.: 0.5 cm$^3$/100 g) on an empty stomach 6 hours after the unavoidable shocks and for 4 consecutive days, in the morning 30 minutes before the learning session and in the evening between 6 and 7 pm.

The test products are dissolved in distilled water.

The test products are administered at doses of 0.05 mg.kg$^{-1}$/day.

RESULTS:

The test proves that some of the products of the invention significantly reduce the number of avoidance failures, which reflects, for some of the products of the invention, a strong activity of antidepressant type.

EXAMPLE F: STUDY OF THE ANXIOLYTIC ACTIVITY—SO-CALLED LIGHT/DARK CAGE TEST IN MICE

PRINCIPLE:

A study of the anxiolytic effects of the compounds of the invention is proposed, using the light/dark cage test in mice.

PROTOCOL:

This test was developed by Crawley et al. (Pharmacol. Biochem. Behav. 1981, 15 (5), pp. 695–9), then modified and behaviorally validated.

The test involves two cages of equal size (20×20×14 cm) made of PVC. One is brightly lit by a 100 W lamp ("cold" light), the other is darkened. The two cages are separated from each other by means of a small opaque tunnel (5×7 cm). The mice are introduced individually into the dark cage and the time spent by the animals in the lit cage, as well as the number of transitions between the dark cage and the lit cage, are recorded by means of keyboards connected to a computer, over 5 minutes.

Each experimental group comprises at least 15 animals.

RESULTS:

The intraperitoneal administration of certain products of the invention results in an increase in the time spent by the mice in the lit cage and in the number of transitions between the dark cage and the lit cage.

This significant increase in the two parameters studied shows the noteworthy anxiolytic activity of certain compounds of the invention.

EXAMPLE G: INVESTIGATION INTO AN ANTIARTHRITIC-TYPE ACTIVITY IN RATS

Groups of 5 male or female Lewis rats weighing 130 to 150 g are used. A suspension of 0.3 mg of killed Mycobacterium tuberculosis in 0.1 cm$^3$ of mineral oil (complete Freund adjuvant, CFA) is administered into the subplantar region of the right hind foot on day 1. The volumes of the hind feet are measured by displacement of water on days 0, 1, 5, 14 and 18. The rats are weighed on days 0 and 18. The products to be tested are suspended in carboxymethylcellulose and are administered orally for 5 consecutive days, from days 1 to 5.

In parallel, a control group is used in order to eliminate artefacts resulting from the handling of the animals. A group treated with a reference product permits validation of the test.

The products of the invention possess a strong inhibitory action in this model, which makes them very advantageous candidates for the treatment of arthritis.

EXAMPLE H: PHARMACEUTICAL COMPOSITION INTENDED FOR THE TREATMENT OF CENTRAL NERVOUS SYSTEM DISORDERS

Tablets containing a 0.1 mg dose of 3-methyl-6-[2-(4-benzylpiperid- 1-yl)ethyl]benzothiazolinone. Formula for 10,000 tablets:

| | |
|---|---|
| 3-Methyl-6-[2-(4-benzylpiperid-1-yl)ethyl]-benzothiazolinone | 1 g |
| Wheat starch | 75 g |
| Corn starch | 75 g |
| Lactose | 325 g |
| Magnesium stearate | 10 g |
| Silica | 5 g |
| Hydroxypropyl cellulose | 10 g |

EXAMPLE I: PHARMACEUTICAL COMPOSITION INTENDED FOR THE TREATMENT OF INFLAMMATORY DISORDERS OF IMMUNE ORIGIN

Tablets containing a 10 mg dose of 3-methyl-6-{4-[N-(2-piperid-1-ylethyl)-N-methylamino] butyl}benzothiazolinone. Formula for 10,000 tablets.

| | |
|---|---|
| 3-Methyl-6-{4-[N-(2-piperid-1-ylethyl)-N-methylamino]butyl}benzothiazolinone | 100 g |
| Wheat starch | 275 g |
| Corn starch | 275 g |
| Lactose | 825 g |
| Magnesium stearate | 10 g |
| Silica | 5 g |
| Hydroxypropyl cellulose | 10 g |

We claim:

1. A compound which is selected from those of formula (I):

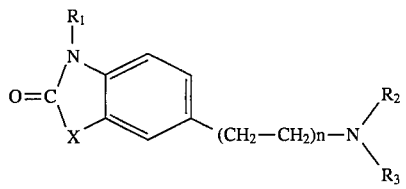

in which:

$R_1$ represents hydrogen or alkyl, n represents 1 or 2,

X represents oxygen or sulfur, $R_2$ represents hydrogen or alkyl, and $R_3$ represents the group —$(CH_2)_m$—$R_4$ in which:

m represents 1, 2, 3 or 4, and $R_4$ represents a group selected from cycloalkylamino, dicycloalkylamino, N-cycloalkyl-N-alkylamino and a heterocyclic radical of formula:

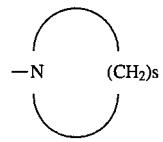

wherein s is six (6), which is unsubstituted or substituted with a radical selected from aryl, arylalkyl, substituted aryl, and substituted arylalkyl, or alternatively $R_2$ forms, with $R_3$ and the nitrogen atom which bears them, a group:

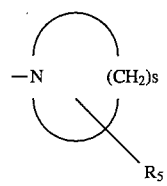

wherein is six (6), wherein the substituent $R_5$ is chosen from aryl, arylalkyl, substituted aryl, and substituted arylalkyl, term "substituted", used reference to the "aryl" and "arylalkyl" radicals, meaning that these groups are substituted with one or more groups chosen from halogen, alkyl, hydroxyl, alkoxy, and trifluoromethyl, the terms "alkyl" and "alkoxy" denote linear or branched groups containing 1 to 6 carbon atoms, inclusive the term "aryl" represents a phenyl or naphthyl group, the term "cycloalkyl" denotes a group of 3 to 9 carbon atoms, inclusive the optical isomers thereof and the addition salts thereof with a pharmaceutically-acceptable acid and, when $R_1$ represents a hydrogen atom, with a pharmaceutically-acceptable base.

2. A compound of claim 1 selected from which is 3-methyl-6-{2-[N-( 2-perhydroazepin-1-yl-ethyl)-N-methylamino]ethyl}benzothiazolinone and an addition salt thereof with a pharmaceutically-acceptable acid.

3. A compound of claim 1 selected from 3-methyl-6-{4-[N-( 2-perhydroazepin-1-yl-ethyl)-N-methylamino] butyl}benzothiazolinone and an addition salt thereof with a pharmaceutically-acceptable acid.

4. A pharmaceutical composition suitable for treating an inflammatory disease or arthritis containing an effective amount of a compound of claim 1 or, where appropriate, one of the addition salts thereof with a pharmaceutically-acceptable acid or base, in combination with one or more excipients.

5. A method of treating a mammal afflicted with an inflammatory disease or arthritis comprising the step of administering to said mammal an amount of a compound of claim 1, which is effective for alleviating said condition.

* * * * *

UNITED STATES PATENT AND TRADEMARK OFFICE
CERTIFICATE OF CORRECTION

PATENT NO. : 5,534,511
DATED : July 9, 1996
INVENTOR(S) : Ange Mouithys-Mickalad, Patrick Depreux, Daniel Lesieur, Gerard Adam, Daniel-Henri Caignard, Pierre Renard, Marie-Claire Rettori It is certified that error appears in the above-indentified patent and that said Letters Patent is hereby corrected as shown below:

Title Page, [56] References Cited, U.S. Patent Documents, Column 2: "5,322,849" should read -- 5,322,843 --.

Column 1, line 9: Delete the "-" (dash) at end of line and insert -- ) --.

Column 1, line 10: Delete the ")" at beginning of the line.

Column 1, line 12: Delete the "-" (dash) at end of line and insert -- ) --.

Column 1, line 13: Delete the ")" at beginning of the line.

Column 3, line 11: "(2-piperid-1-yl-ethy-" should read -- (2-piperid-1-yl-ethyl) --.

Column 3, line 12: Delete "l)" at beginning of the line.

Column 3, line 17: Delete the "-" (dash) at end of line and insert -- ) --.

Column 3, line 18: Delete ")" at beginning of the line.

Column 3, line 19: "(4-phenylpiperid-1    -yl)" should read -- (4-phenylpiperid-1-yl) --.

UNITED STATES PATENT AND TRADEMARK OFFICE
CERTIFICATE OF CORRECTION

PATENT NO. : 5,534,511
DATED : July 9, 1996
INVENTOR(S) : Ange Mouithys-Mickalad, Patrick Depreux, Daniel Lesieur, Gerard Adam, Daniel-Henri Caignard, Pierre Renard, Marie-Claire Rettori It is certified that error appears in the above-indentified patent and that said Letters Patent is hereby corrected as shown below:

Column 3, line 21: "3-methyl-6-{4-N-" should read -- 3-methyl-6-{4[-N- --.

Column 3, line 24: Delete the "-" (dash) at end of line and insert -- ) --.

Column 3, line 25: Delete ")" at beginning of the line.

Column 5, line 59: "2;36" should read -- 236 --.

Column 6, line 67: "Procedure:" should go at top of

Column 7 as line 1.

Column 8, line 67: "Procedure:" should go to top of Column 9 as line 1.

Column 10, lines 66 and 67: Move to top of Column 11 as lines 1 and 2. Delete "continued".

Column 13, line 60: "DMSO-d6):" should read -- DMSO-$d_6$: --.

Column 17, line 49: Delete "-" (dash) at end of line and insert -- ) --.

Column 17, line 50: Delete ")" from beginning of the line.

UNITED STATES PATENT AND TRADEMARK OFFICE
CERTIFICATE OF CORRECTION

PATENT NO. : 5,534,511

DATED : July 9, 1996

INVENTOR(S) : Ange Mouithys-Mickalad, Patrick Depreux, Daniel Lesieur, Gerard Adam, Daniel-Henri Caignard, Pierre Renard, Marie-Claire Rettori It is certified that error appears in the above-indentified patent and that said Letters Patent is hereby corrected as shown below:

Column 20, line 57: Delete "{" from end of line.

Column 20, line 58: Insert "{" at beginning of line.

Column 28, line 31: Insert -- s -- after "wherein".

Column 28, line 33: "term "substituted", used reference" should read -- the term "substituted", used in reference --.

Column 28, line 38: Insert -- , -- (comma) after "inclusive".

Column 28, line 41: Insert -- , -- (comma) after "inclusive".

UNITED STATES PATENT AND TRADEMARK OFFICE
CERTIFICATE OF CORRECTION

PATENT NO.   : 5,534,511
DATED        : July 9, 1996
INVENTOR(S)  : Ange Mouithys-Mickalad, Patrick Depreux, Daniel Lesieur, Gerard Adam, Daniel-Henri Caignard, Pierre Renard, Marie-Claire Rettori It is certified that error appears in the above-indentified patent and that said Letters Patent is hereby corrected as shown below:

Column 28, line 46:   Delete "which is".

Column 28, line 47:   Delete excessive space in the line.

Column 28, line 51:   Delete excessive space in the line.

Signed and Sealed this

Eighth Day of October, 1996

Attest:

BRUCE LEHMAN

Attesting Officer           Commissioner of Patents and Trademarks